United States Patent [19]

Ku et al.

[11] Patent Number: 4,496,765
[45] Date of Patent: Jan. 29, 1985

[54] PREPARATION OF 2-(METHYLTHIOMETHYL)-6-(TRIFLUOROMETHYL)ANILINE FROM ORTHO-AMINOBENZOTRIFLUORIDE

[75] Inventors: Audrey Y. Ku, Chesterfield; John P. Chupp, Kirkwood; Terry M. Balthazor, University City, all of Mo.

[73] Assignee: Monsanto Company, St. Louis, Mo.

[21] Appl. No.: 530,153

[22] Filed: Sep. 7, 1983

[51] Int. Cl.$^3$ .............................................. C07C 85/24
[52] U.S. Cl. .................................................. 564/440
[58] Field of Search ......................................... 564/440

[56] References Cited

U.S. PATENT DOCUMENTS

| | | | |
|---|---|---|---|
| 3,894,034 | 7/1975 | Gassman | 564/440 UX |
| 3,954,797 | 5/1976 | Gassman | 564/440 UX |
| 3,960,926 | 6/1976 | Gassman | 564/440 UX |
| 3,985,756 | 10/1976 | Gassman | 564/440 UX |
| 4,035,375 | 7/1977 | Gassman | 564/440 UX |
| 4,172,095 | 10/1979 | Steinman et al. | 564/440 |

OTHER PUBLICATIONS

Claus, Tetrahedron Letters, p. 3607 (1968).
Gassman, Tetrahedron Letters, p. 497 (1972).
Johnson, Tetrahedron Letters, p. 501 (1972).
Vilsmaier, Tetrahedron Letters, p. 625 (1972).
Claus & Vilsmaier, Tetrahedron Letters 31, p. 505 (1975).
Claus, et al., Phosphorus and Sulfur, 1, pp. 11, 18 (1976).

*Primary Examiner*—Paul F. Shaver
*Attorney, Agent, or Firm*—Robert B. Martin; Richard H. Shear

[57] ABSTRACT

This invention relates to a process for the preparation of 2-(methylthiomethyl)-6-(trifluoromethyl) aniline, [MTA], from ortho-aminobenzotrifluoride, (OABT), employing a single solvent transformation via a sulfilimine intermediate. A sulfilimine hydrochloride salt is prepared by the oxidative addition of dimethyl sulfide to OABT in the presence of N-chlorosuccinimide. Neutralization of the sulfilimine hydrochloride salt with aqueous sodium hydroxide followed by phase separation results in an organic phase containing free sulfilimine and an aqueous phase generally containing succinimide and/or sodium succinimide. In a preferred embodiment the phase separation is performed in such a manner to leave a catalytic amount of succinimide in the organic phase. The free sulfilimine catalytically rearranges at moderate temperatures in the presence of this succinimide catalyst to form MTA. The aqueous phase separated after neutralization of the sulfilimine hydrochloride salt contains succinimide and/or sodium succinimide which may be converted by the action of chlorine to N-chlorosuccinimide which in turn may be recycled to the first step in the process.

14 Claims, No Drawings

PREPARATION OF 2-(METHYLTHIOMETHYL)-6-(TRIFLUOROMETHYL)ANILINE FROM ORTHO-AMINOBENZOTRIFLUORIDE

BACKGROUND OF THE INVENTION

1. Field of the Invention

This invention relates to a process for the preparation of 2-(methylthiomethyl)-6-(trifluoromethyl) aniline [MTA] from ortho-aminobenzotrifluoride [OABT].

2. Description of the Prior Art

The preparation of ortho-(methylthiomethyl) anilines from the corresponding anilines via sulfilimine intermediates is known. Claus, Tetrahedron Letters, p. 3607 (1968), describes the preparation of aromatic sulfilimines from anilines and dimethylsulfoxide in the presence of $P_2O_5$ in a base such as triethylamine. Claus also discloses thermal rearrangement of these sulfilimines to ortho-(methylthiomethyl) anilines. See also, Gassman, Tetrahedron Letters, p. 497 (1972) and Johnson, Tetrahedron Letters, p. 501 (1972). Gassman discloses the use of N-t-butyl anilines to generate N-t-butyl-N-chloro anilines, generally employing an alkyl-hypochlorite and subsequently sulfilimine salts with dimethyl sulfide which, upon treatment with a base under anhydrous conditions, were converted to N-substituted ortho-(methylthiomethyl) anilines. Vilsmaier, Tetrahedron Letters, p. 625 (1972) describes the reaction of anilines with dimethyl sulfide and N-chlorosuccinimide to form sulfilimine hydrochloride salts. Vilsmaier here does not teach the rearrangement of the sulfilimine or its salt. Another method of preparation of sulfilimine salts is disclosed in Claus and Vilsmaier, Tetrahedron Letters 31, p. 505 (1975). This article, like the previous Vilsmaier article, discloses the reaction of anilines with dimethyl sulfide in the presence of N-chlorosuccinimide to form the sulfilimine hydrochloride salt. In the Claus and Vilsmaier reference the sulfilimine hydrochloride salt is neutralized with aqueous caustic but Claus and Vilsmaier do not disclose the rearrangement of the sulfilimine produced by this process. See also Gassman U.S. Pat. Nos. 3,894,034, 3,954,797, 3,960,926, 3,985,756 and 4,035,375. The Gassman patents generally relate to the preparation and essentially anhydrous rearrangement of sulfilimine salts to produce ortho-(methylthiomethyl) anilines. Claus, et al., Phosphorus and Sulfur, 1, pp. 11, 18 (1976) (and references cited therein) and U.S. Pat. No. 4,172,095 describe sulfilimine rearrangement in the presence of alchohols such as ethanol or t-butanol.

The prior art processes for preparing ortho-(methylthiomethyl) anilines via the sulfilimine route generally exhibit a number of drawbacks which make them undesirable for commercial scale conversion processes. These prior art sulfilimine formation and rearrangement reactions proceed satisfactorily at the laboratory scale but they employ reagents which are expensive, often dangerous, and difficult to work with on a larger scale. One of the most serious of these drawbacks is the generally held requirement for processing under anhydrous conditions and utilizing dry organic bases such as tertiary amines. Moreover, the rearrangement of sulfilimines to ortho-(methylthiomethyl) anilines was thought to require high temperatures, the presence of alchohols or dry basic catalysts such as triethylamine.

Accordingly it is an object of the present invention to provide a process for the smooth and efficient conversion of ortho-aminobenzotrifluoride to MTA which substantially avoids the drawbacks of the prior art.

More specifically, it is an object of the present invention to provide a process for the conversion of OABT to MTA in which the overall conversion process is carried out in a single common organic solvent.

It is another object of the present invention to provide a process for the conversion of OABT to MTA in which inexpensive aqueous caustic solution is utilized to neutralize the sulfilimine hydrochloride salt formed and to extract at least a major portion of succinimide formed.

It is also an object of the present invention to provide a process for converting OABT to MTA having improved economies by virtue of conversion of aqueous succinimide by-products to N-chlorosuccinimide for recycle to the sulfilimine hydrochloride salt preparation step.

It is a further object of this invention to provide a process for the conversion of OABT to the MTA in which no alcohols or dry organic bases are utilized in either neutralization of the sulfilimine hydrochloride salt or its rearrangement.

It is another object of this invention to include only a minor (catalytic) amount of succinimide when rearranging the neutral sulfilimine.

SUMMARY OF THE INVENTION

In accordance with the foregoing objectives and others which will be readily apparent to those skilled in the art, the present invention provides a process for preparing 2-(methylthiomethyl)-6-(trifluoromethyl) aniline, which process comprises the steps of (a) reacting ortho-aminobenzotrifluoride with dimethyl sulfide and N-chlorosuccinimide in an inert solvent to produce N-(2-trifluoromethylphenyl)-S,S,-dimethyl sulfilimine hydrochloride and succinimide; (b) treating said sulfilimine hydrochloride with aqueous base to neutralize said sulfilimine hydrochloride to N-(2-trifluoromethylphenyl)-S,S-dimethyl sulfilimine and to dissolve at least a major portion of succinimide product in the aqueous phase; (c) separating the organic phase produced in step (b) containing said neutral sulfilimine from the aqueous phase containing said succinimide product; (d) subjecting said neutral sulfilimine in said organic phase to catalytic rearrangement at moderate temperatures in the presence of a minor amount of succinimide to form 2-(methylthiomethyl)-6-(trifluoromethyl) aniline; (e) reacting said succinimide product in said aqueous phase with chlorine to produce N-chlorosuccinimide; and (f) recycling said N-chlorosuccinimide produced in step (e) for use as a reagent in step (a).

MTA has a wide variety of known uses including use as starting materials in the production of specific ortho-methyl anilines which can be used, inter alia, in the manufacture of herbicides and the like.

Useful herbicidal compounds can be prepared by first converting MTA to the corresponding ortho-(chloromethyl) aniline or its anilinium salt as described in commonly assigned copending application Ser. No. 358772 entitled "Manufacture of Ortho-Methyl Anilines From Ortho-Amino Benzyl Sulfoxides" filed on Mar. 17, 1982, in the names of Chupp et al. The ortho-(chloromethyl)aniline or its anilinium salt can then be converted to the corresponding 2'-methyl-2-haloacetanilide by the process described in commonly assigned copending application Ser. No. 530,154 entitled "Preparation of 2'-Methyl-2-Haloacetanilides" filed on even date herewith in the names of Chupp and Miller. Finally, the desired herbicide can be produced using the N-alkylation process described in Chupp et al U.S. Pat. No. 4,258,196.

DETAILED DESCRIPTION OF THE INVENTION

The first step of the process of the present invention involves the reaction of OABT with N-chlorosuccinimide (NCS) and dimethyl sulfide (DMS) to produce the corresponding sulfilimine hydrochloride salt and succinimide.

The reagents may be provided in essentially stoichiometric amounts, although molar excesses of one or more of the reagents may be employed if desired. Large excesses of NCS should be avoided, however. In the preferred embodiment, slight excesses of NCS and DMS relative to OABT are employed. This reaction is carried out in an inert organic solvent. A wide variety of inert organic solvents and diluents may be employed, including, for example, methylene chloride, toluene, and ethylene dichloride. Protic solvents, i.e., solvents having a proton available for hydrogen bonding, should be avoided. The preferred inert organic solvent is methylene chloride.

The reaction of OABT, NCS and DMS in methylene chloride is a rapid and exothermic reaction. In general, the reaction should be run at relatively low temperatures, i.e., from about 10° C. up to about 40° C. If the reaction temperature is allowed to exceed about 20° C., the power of NCS as a chlorinating agent may result in undesirable ring chlorination. In a preferred embodiment it is desired to keep the reaction temperature between 0° and about 10° C. The reactants may be combined in any convenient manner in any suitable reaction vessel. For example, solid NCS may be added directly to a mixture of OABT and DMS in methylene chloride. When employing this approach, a portion of the NCS charge is added to the reaction mixture which then exotherms followed by a return to a proper temperature. Subsequent additions of NCS until a full charge amount is added can be provided in the same manner. In the preferred embodiment the reactants are combined by first mixing NCS and OABT with methylene chloride and cooling the mixture to 0° C. DMS, preferably in admixture with methylene chloride, is then added at such a rate that the reaction is kept between 0° and 10° C. Generally, DMS addition is completed in about 25–30 minutes.

After all the reactants are combined, the reaction as described above proceeds relatively rapidly and in general will be completed in times ranging from about 10 to 20 minutes. In general, protracted reaction times are avoided since long reaction times are accompanied by an increase of undesirable side reactions.

In addition to the sulfilimine hydrochloride salt, other reaction products and by-products include succinimide, unreacted OABT, and small amounts of ring chlorination products. Typically, yields of about 90% to 94% of sulfilimine hydrochloride are achieved with about 3% to 7% of unreacted OABT. As described hereinafter, this unreacted OABT can be recovered at the end of the overall process and recycled back to the first step to improve overall yields.

The next step in the process of the present invention is the neutralization with aqueous base of the sulfilimine hydrochloride salt produced in the first step. Although NaOH is preferred, other alkali or alkaline earth metal hydroxides or carbonates can be employed.

As indicated above, in those prior art processes having a final objective of sulfilimine rearrangement, the sulfilimine salts were typically neutralized with a dry base such as triethylamine. Others, without specifically reciting the neutralization, rearranged the sulfilimine salt in the presence of a dry organic base which was said to catalyze the rearrangement. Despite the teachings of the art that the rearrangement should be effected under substantially anhydrous conditions, applicants have discovered that neutralization of the sulfilimine salt with aqueous base, for example, aqueous sodium hydroxide followed by simple phase separation and without the necessity of completely drying the organic phase results in a pathway leading to catalytic rearrangement and regeneration of initial reagents (i.e., NCS) which is extremely advantageous over the processes described in the prior art. The aqueous caustic reagent of the present invention is less expensive than the organic bases employed in the prior art, and, importantly, permits the safe regeneration of NCS from the succinimide product by chlorination without the formation of dangerous and explosive side products such as $NCl_3$.

Sulfilimine hydrochloride that is formed from OABT, NCS and DMS is rapidly hydrolyzed to OABT and dimethyl sulfoxide by water, aqueous acid or less than stoichiometric amounts of aqueous base. Using adequate amounts of aqueous alkali solution, however, will ensure that the sulfilimine hydrochloride is rapidly neutralized to sulfilimine without significant hydrolysis. In practice aqueous solutions containing about 5 to 20% by weight of sodium hydroxide are preferred with the most preferred reagent being 5 to 10% sodium hydroxide solutions. Amounts of 5% sodium hydroxide equal to a molar equivalent have been found to effect the neutralization reaction rapidly without substantial hydrolysis. The addition of sodium hydroxide in molar ratios that exceed about 2 equivalents of NaOH per equivalent of sulfilimine salt may result in complete extraction of succinimide into the aqueous layer, which is undesirable when the succinimide is to be carried forward into the organic phase as a catalyst for the rearrangement according to the preferred embodiment as described hereafter. A high final pH, i.e., ca. 12, is generally to be avoided, however, as these aqueous solutions, on standing, can cause considerable hydrolysis of solute succinimide.

It is also important to effect the neutralization reaction rapidly with good mixing. While the neutralization reaction will proceed over a broad range of temperatures, it is preferred to employ relatively low temperatures, i.e., in the range from about 10° to 25° C. While the reactants may be combined in any suitable fashion, in the preferred embodiment the sulfilimine hydrochloride salt is added rapidly with vigorous stirring to a cooled reactor containing the aqueous sodium hydroxide solution. The neutralization reaction proceeds relatively quickly and typically is complete in from about 3 to 5 minutes although longer or shorter times may be employed. The neutral sulfilimine is very stable toward water or base.

Upon neutralization of the sulfilimine hydrochloride with aqueous sodium hydroxide, a major portion of the succinimide is extracted into the aqueous layer. Depending upon the quantity of caustic used in the neutralization (i.e., the pH of the extracted aqueous phase), the aqueous layer will contain sodium succinimide or succinimide or both. For example, at a pH above about 12, the succinimide product is dissolved in the aqueous phase predominately as sodium succinimide. Unless otherwise specified, the terms succinimide solution or succinimide product, as used herein are intended to include succinimide, sodium succinimide or mixtures thereof.

In the broad practice of this invention, the sulfilimine can be recovered from the organic phase in essentially pure form by vacuum evaporation at ambient temperature, trituration of the residue in an appropriate solvent (e.g., hexane or heptane), filtration and air drying. The minor amount of succinimide needed to catalyze the rearrangement reaction can then be added to the pure sulfilimine to prepare the reaction mixture. Although the sulfilimine can be isolated in good yield and rearranged as described, the single solvent, non-isolation process of the preferred embodiment of the present invention has marked advantages. Since sulfilimines can undergo appreciable autogenous exothermic rearrangement above about 100° C., and even lower temperatures in the presence of catalysts, e.g., succinimide, storage of pure isolated sulfilimine products in the absence of solvent could pose a significant safety problems.

The next step in the process of the present invention is the separation of the organic and aqueous phases produced in the neutralization step just described. In this step, the neutral sulfilimine, preferably including a portion of succinimide sufficient to catalyze the subsequent rearrangement step, remains in the organic phase while most of the succinimide is extracted in the aqueous phase. Applicants have unexpectedly discovered that a facile phase separation without the need for any drying steps results in an organic phase which contains minor catalytic amounts of succinimide along with the neutral sulfilimine. The economics of the process step are enhanced by the regeneration and recycle of NCS which can be regenerated, as described below, by chlorination of the aqueous phase recovered.

The preferred procedure for effecting the phase separation is as follows. The neutralization reaction mixture can be simply allowed to stand for a period of time sufficient for the aqueous and organic layers to separate. In general, this phase separation takes place rapidly and will be substantially complete in from about 10 to 30 minutes. Typically, about 20 minutes is suitable for phase separation. The organic layer can be separated from the aqueous layer by any known techniques such as decanting and the like. Care should be taken to avoid extraction of excess amounts of water in the organic layer.

The amount of succinimide remaining in the organic layer will depend to a certain extent on the amount of aqueous base, for example, sodium hydroxide solution, employed for the neutralization step. For example, when sulfilimine hydrochloride mixture is neutralized with one equivalent of sodium hydroxide solution, the organic layer will contain about 15 to 20% succinimide while the aqueous layer will contain 80 to 85% of the succinimide. Increasing the amount of caustic will increase the amount of succinimide which is extracted in the aqueous layer. When two equivalent amounts of caustic are used, substantially all of the succinimide is extracted, although rapid downward pH adjustment is necessary to prevent hydrolysis of solute succinimide.

Control of the amount of succinimide remaining in the organic phase is also effected by the manner in which the organic phase is subsequently washed. After neutralizing the sulfilimine hydrochloride mixture with about one equivalent of aqueous sodium hydroxide solution, the recovered organic layer is typically washed twice with a small amount of additional caustic and once with water. In a batch system, the washings are performed by vigorous shaking for 1 to 2 minutes. To improve the recovery of sulfilimine, the original aqueous layer and the aqueous washes are then combined and backwashed with methylene chloride. The recovered organic phase is then added to the original organic sulfilimine solution. At this point, the organic solution preferably contains approximately two mol percent succinimide. In the broad practice of this invention, the washing operation can also be carried out in a continuous fashion using known arrangements such as serially arranged mixer-settlers, counter-current extraction columns and the like.

The next step in the process of the present invention is the catalytic rearrangement of the neutral sulfilimine to MTA.

The prior art describes the rearrangement of aromatic sulfilimine compounds to ortho-(methylthiomethyl) anilines either at elevated temperature, in the presence of alcohols or in the presence of an organic base catalyst. The use of alcohols is generally undesirable in that it can lead to cleavage reactions which result in the formation of dimethyl sulfoxide and OABT. The present invention is based in part on the discovery that neutral succinimide functioning as an acid-base catalyst in amounts of about 1 to 10% by weight of the sulfilimine catalyzes the rearrangement reaction permitting the reaction to proceed at intermediate temperature and/or shorter reaction times. As indicated above, the single solvent sulfilimine salt formation and aqueous neutralization process according to the present invention provides an ideal starting reagent for the rearrangement reaction, since the organic sulfilimine extract can be controlled to include the precise catalytic amounts of succinimide required. While the presence of minor amounts of water or aqueous sodium hydroxide in the organic phase will in fact cause competitive hydrolysis of the sylfilimine, the overall advantages achieved by this process outweigh any disadvantages.

The catalyzed rearrangement step can be carried out over a wide range of temperatures and pressures. Typically, intermediate temperatures in the range of about 35° to 110° C. are preferred. At these conditions, the rearrangement reaction is completed in about 0.5–20 hours, depending upon temperature, succinimide catalyst and reactant concentrations. Alternatively, a solution of sulfilimine, including, e.g., methylene chloride as a solvent, can be heated for short periods under pressure (i.e., autogenous to about 1000 psig) at 120°–180° C. to effect rearrangement. Catalyzed rearrangement temperatures of about 110° to 210° C. decrease the rearrangement times to a matter of minutes, with specific times depending upon temperature, catalyst and reactant concentrations. The succinimide-containing organic phase separated in the previous step can typically be heated at 80°–110° C. for about 75 to 85 minutes, preferably for about 2 to 4 hours. At this stage the rearrangement should be completed.

Yields in the rearrangement reaction are typically about 70 to 80% MTA and 10 to 15% OABT. In addition, small amounts of by-products including chlorinated OABT and MTA are also present. The MTA rearrangement product may be purified by distillation.

Prior to effecting this distillation or other treatment, succinimide can be conveniently removed as desired by washing the organic phase with aqueous base, preferably sodium hydroxide solution. The presence of succinimide or succinamic acid may result in decomposition of MTA during purification by distillation. Organic solvent; e.g., methylene chloride, can be removed from the washed organic phase by distillation at room temperature under reduced pressure. The OABT can be separated from MTA by distillation under reduced pressure. In a preferred embodiment, the recovered OABT is recycled for reaction with DMS and NCS. In this way, high overall yields of MTA from OABT are possible.

It is also an important aspect of the process of the present invention to regenerate NCS from the separated succinimide-containing aqueous phase and to recycle this NCS to the sulfilimine formation step.

As indicated above, the separated aqueous phase may contain from about 80 to 98% of the succinimide produced in the sulfilimine salt forming reaction. If the aqueous layer obtained from the neutralization of the sulfilimine hydrochloride salt is stored, it should be stored in neutral or slightly acidic aqueous solution since succinimide is very unstable in sodium hydroxide solution. At the time that NCS regeneration is effected, sodium hydroxide is preferably added continuously and simultaneously with chlorination of the aqueous succinimide solution, while carefully controlling the pH at about 3.0. In order to avoid excessive decomposition of the succinimide and low yields of NCS, NCS regeneration should preferably be performed as soon as possible after recovering the aqueous phase.

Typically, the NCS regeneration step is carried out at relatively low temperatures, i.e., from about 0° to 20° C. and preferably about 0° to 10° C. Contact of the aqueous succinimide solution with $Cl_2$ can be effected by bubbling chlorine gas through the system. Typical yields of NCS are in the range of about 70 to 95% based on the starting NCS with assays of 95% or better. NCS product suitable for recycle to the first step of the process can be recovered from the chlorination step by filtration and air drying. While essentially stoichiometric amounts of the reagents can be employed, it is preferred to use excess sodium hydroxide relative to the succinimide present. Typically, from about 1.02 to 1.2 equivalents of NaOH per equivalent of succinimide can be employed. Similarly, chlorine is generally employed in molar excess as compared to succinimide. Typically, from about 1.2 to 2.2 equivalents of $Cl_2$ per equivalent of succinimide are employed. Reaction times for the chlorination step run from about 0.75 to 1.5 hours and preferably about one hour. After chlorination is completed, sparging of excess chlorine with a small stream of nitrogen can be effected. After filtration of the NCS product, the filtrate should be treated immediately with a reducing agent; i.e., sodium thiosulfate, and properly disposed so as to minimize the formation of dangerous and explosive $NCl_3$.

The regeneration step of the present invention is particularly facilitated by the absence of any organic amine bases which avoids the problem of formation of dangerous chlorine containing compounds such as $NCl_3$ during the chlorination regeneration step.

The following examples are included to better illustrate the practice of this invention. These examples are included for illustrative purposes only and are not in any way intended to limit the scope of the invention.

EXAMPLE 1

This example describes a procedure for preparing and isolating pure N-(2-trifluoromethylphenyl)-S,S-dimethyl sulfilimine. NCS (40.7 g), methylene chloride (150 ml) and OABT (48.3 g) were added to a 500 ml flask. The reaction mixture was cooled to 0° C. and 23 ml of dimethyl sulfide in admixture with 40 ml of methylene chloride was added. The temperature of the mixture was kept below 10° C. during addition. After adding all of the dimethyl sulfide, cooling was terminated and the reaction mixture was stirred an additional 20 minutes. 10% sodium hydroxide (0.246 mol) was then quickly added to neutralize the reaction mixture. An organic phase was then separated from an aqueous phase. The organic phase was concentrated using a vacuum rotary evaporator at ambient temperature condition. The organic residue was then triturated with hexane to give an insoluble solid which was filtered and air dried to give 62.5 g (94%) of colorless sulfilimine, melting point 97° to 98° C. Analysis calculated for $C_9H_{10}F_3NS$: C, 48.86; H, 4.56; S, 14.49; Found: C, 48.74; H, 4.60; S, 14.50. The filtrate was concentrated to yield 3.1 g of oil, containing 76% OABT.

EXAMPLE 2

This example describes attempts at rearranging the sulfilimine produced in Example 1 with and without the presence of succinimide. Sulfilimine (4.42 g) prepared in accordance with Example 1, was slurried in 10 ml of heptane and heated at reflux. After 1 hour at reflux, nuclear magnetic resonance (NMR) spectroscopy indicated that less than 10% rearrangement had occurred. Succinimide (0.1 g) was added to the cooled reaction mixture and upon reheating to reflux, the sulfilimine was completely rearranged to MTA in less than about 10 minutes as verified by NMR spectroscopy.

EXAMPLE 3

This example describes attempts at rearranging the sulfilimine produced in Example 1 with and without the presence of succinimide. Succinimide-free sulfilimine produced in Example 1 was heated at reflux in cyclohexane for about 4 hours. Fluorine NMR spectroscopy showed that no significant amounts of MTA were formed during this time. Succinimide (0.5 mol percent) was then added to the reaction mixture. Reflux was continued, and after about 3 hours rearrangement was complete as indicated by fluorine NMR spectroscopy.

EXAMPLE 4

This example describes the non-catalytic (thermal) rearrangement of sulfilimine produced in Example 1 in xylene. Pure sulfilimine produced as described in connection with Example 1 was heated with 89 ml of mixed xylenes. Fluorine NMR monitoring indicated that complete rearrangement occurred in about 4 hours, while the temperature decreased from about 142° to 137° C.

EXAMPLE 5

This example describes a preferred procedure for preparing N-(2-trifluoromethylphenyl)-S,S-dimethyl sulfilimine containing a small (catalytic) amount of succinimide. A dry 3 L reactor equipped with thermometer, mechanical stirrer and facility for cooling is charged with 269 g (2.01 mol) of N-chlorosuccinimide and 750 ml of methylene chloride. Stirring is started and 322.2 g (2.00 mol) of OABT is added. The resulting slurry is then cooled to 0° C. (an ice-acetone bath is used) and a solution of 126.5 g (2.036 mol) of dimethyl sulfide in 50 ml of methylene chloride is added over 25–30 minutes keeping the reaction temperature at 0°–5° C. The reaction is exothermic and should be maintained below 5° C. by use of efficient cooling and by control of the DMS addition rate. When approximately half of the DMS has been added, the slurry will give way to a cloudy solution. After completion of the addition, the cooling bath is removed and the reaction mixture is stirred without cooling for 10 to 15 minutes.

The sulfilimine hydrochloride is then neutralized by rapid addition of the cloudy solution to 1010 g of 8% NaOH (2.02 mol) cooled to 10° C. with stirring. The two-phase mixture is stirred for 3 minutes and the layers are allowed to separate over 10–20 minutes.

The organic layer containing the sulfilimine and 10–15% of formed succinimide is separated from the aqueous phase. The aqueous layer (containing 85–90% of the succinimide formed in the reaction) is washed once with 500 ml of methylene chloride to remove any sulfilimine remaining in the aqueous layer. The layers are allowed to separate over 10 minutes and the lower organic layer is drawn off and combined with the previously separated organic layer. The combined organic solution is washed twice with 300 g of 1% NaOH and once with 200 ml of water. After careful layer separation, an organic solution is recovered containing sulfilimine.

The original aqueous layer and all aqueous washes are combined and washed with 300 ml of methylene chloride. The organic layer is then added to the organic solution above. The resulting organic solution contains the sulfilimine product and approximately 2 mol percent of succinimide. The aqueous layer is reserved for regeneration of NCS.

EXAMPLE 6

This example describes a procedure for rearranging the sulfilimine produced in Example 5 to MTA. The organic solution (1900–2000 ml) containing sulfilimine, methylene chloride, low boilers and some dissolved water is transferred to a 3 L flask equipped for distillation. The mixture is distilled at atmospheric pressure removing 900–1000 ml of material (mostly methylene chloride and water) over the course of one hour to a final volume of approximately 1000 ml. The sulfilimine solution darkens somewhat to a brownish color from its original orange to light brown color during the course of the distillation. The solution is then cooled to room temperature in preparation for rearrangement.

To a 2 L round bottom flask equipped with mechanical stirrer, thermometer, addition funnel and distillation head, 500 ml of toluene is added. The stirred toluene is then heated to boiling (110° C.). When the toluene begins to boil, the sulfilimine solution is added at a rate of about 12 ml/min. The pot temperature will begin to fall and a mixture of methylene chloride and toluene will distill from the reaction (should be at approximately the same rate as the sulfilimine solution addition rate). The pot temperature should be maintained above 80° C. by control of the sulfilimine addition rate and by external heating. After approximately one-half of the sulfilimine solution has been added (approximately 40 to 45 minutes), the pot temperature will begin to rise slowly even though the rate of addition and external heating remain constant. This is an indication that the rearrangement has started. The rate of addition of the sulfilimine solution can be increased slightly at this point so that addition of the second half of the sulfilimine solution requires 30 to 35 minutes. In the latter part of the addition, the pot temperature will rise and should be kept at or below 110° C. by reducing the amount of external heating. When the addition is complete, the pot temperature is allowed to rise to 120° to 125° C. and the dark mixture will slowly turn to a light orange color and solvent distillation will cease. After completion of the rearrangement, the solution is cooled to room temperature.

The crude orange product (500–550 g) containing 10 to 20% toluene, 6 to 8% OABT and 60 to 70% MTA is analyzed by gas chromatography. The yield of OABT is 11 to 13% and that of MTA is 76 to 80%.

EXAMPLE 7

This example describes a procedure for regenerating NCS from the aqueous phase recovered in Example 5. The aqueous layer (1800–2000 ml) containing succinimide is placed in a 5 L flask equipped with chlorine addition tube, mechanical stirrer, caustic addition apparatus, pH probe and ice-water-acetone cooling bath. The clear, colorless solution is adjusted to pH 3.0 by addition of conc. HCl while cooling to 0° C. with stirring. Chlorine is then bubbled into the solution subsurface at the rate of about 2.0 g/min while 30% caustic is simultaneously added at such a rate that the pH is maintained at 2.7 to 3.3 while maintaining the reaction temperature at 0° to 5° C. NCS begins to precipitate after 20 to 30 g of chlorine have been added. When 225.0 g (3.17 mol, 1.58 eq) of chlorine has been added the addition of chlorine and caustic is stopped (total reaction time about 110 minutes), the mixture is stirred for 5 minutes and filtered immediately. The peach-colored solid is washed with 100 ml of ice cold water and is air dried.

The filtrate is immediately treated with 1M sodium thiosulfate solution until a negative test for Cl+ (KI starch paper) is obtained (about 400 to 450 ml are required). The treated filtrate is then immediately disposed.

The weight of air-dried NCS is 260 g which assays 95 to 97%; total recovery is 91%.

EXAMPLE 8

This example describes attempts at rearranging pure sulfilimine in a continuous falling film arrangement with and without catalyst. A solution of pure sulfilimine dissolved in methylene chloride was slowly introduced into the top end of a vertically oriented spiral condenser. The lower end of the condenser was attached to a collection flask. The condenser was 16 inches high. Hot oil, 140° C., was circulated through the shell side of the condenser countercurrently to the downward flow of sulfilimine. The feed rate of the sulfilimine solution was adjusted to give a residence time in the heated condenser of about 3 to 4 minutes. As the sulfilimine solution entered the heated condenser, the solvent was rapidly evaporated. The residual sulfilimine melted and flowed downwardly through the apparatus. After about 20 minutes of continuous operation, the product collected in the collection flask was analyzed by using fluorine NMR spectroscopy. The analysis showed that only 10% of the starting sulfilimine had been rearranged to MTA. Thereafter, the above procedure was identically repeated except that 4 mol percent succinimide was included in the sulfilimine-methylene chloride solution. Under identical temperature and residence times, an analysis of the product collected in the collection flask included 87.5% MTA, 6.7% OABT and less than 1% residual sulfilimine.

EXAMPLE 9

This example describes the falling film rearrangement of sulfilimine derived by treating sulfilimine hydrochloride produced in accordance with Example 5 in a continuous wash system. 2 mol OABT were converted to sulfilimine hydrochloride using the procedure described in Example 5. The crude methylene chloride reaction mixture containing the sulfilimine hydrochloride was then continuously fed to the inlet end of a series of mixer-settler tanks, while countercurrently caustic and water solutions were also continuously introduced. A methylene chloride solution of sulfilimine, containing 3.5% succinimide, was continuously recvered from the countercurrent treatment. The combined aqueous streams recovered from the treatment contained the bulk of the succinimide. This aqueous stream was simultaneously treated with chlorine and sodium carbonate, yielding a 71% recovery of NCS (after filtering and drying). The methylene chloride solution of sulfilimine was separately introduced to the falling film reactor described in Example 8. A product containing 83 mol percent MTA and 11% OABT was recovered from the collector flask.

Since modifications will be apparent to those skilled in the art, it is intended that the invention be limited only by the scope of the appended claims.

We claim:

1. A process for preparing 2-(methylthiomethyl)-6-(trifluoromethyl) aniline, which process comprises the steps of:
   (a) reacting ortho-aminobenzotrifluoride with dimethyl sulfide and N-chlorosuccinimide in an inert solvent to produce N-(2-trifluoromethylphenyl)-S,S-dimethyl sulfilimine hydrochloride and succinimide;
   (b) treating the sulfilimine hydrochloride product with aqueous base to neutralize said sulfilimine hydrochloride to N-(2-trifluoromethylphenyl)-S,S-dimethyl sulfilimine and to form separate aqueous and organic phases, at least a major portion of succinimide product being dissolved in said aqueous phase;
   (c) separating said organic phase containing said neutral sulfilimine from said aqueous phase containing said succinimide product;
   (d) subjecting said neutral sulfilimine in said organic phase to catalytic rearrangement in the presence of a minor amount of succinimide to form 2-(methylthiomethyl)-6-(trifluoromethyl) aniline;
   (e) reacting said succinimide product in said aqueous phase with chlorine to produce N-chlorosuccinimide; and
   (f) recycling said N-chlorosuccinimide produced in step (e) for use as a reagent in step (a).

2. The process according to claim 1 wherein said minor amount of succinimide in step (d) comprises a portion of the succinimide produced in step (a) and not extracted into said aqueous phase in step (b).

3. The process according to claim 1 wherein said aqueous base comprises an aqueous solution of an alkali metal or alkaline earth metal, hydroxide or carbonate.

4. The process according to claim 3 wherein said aqueous base comprises aqueous sodium hydroxide.

5. The process according to claim 1 wherein said organic phase separated in step (c) is sequentially washed with aqueous base and water to dissolve at least a portion of residual succinimide.

6. The process according to claim 1 wherein the catalytic rearrangement of step (d) is conducted at a temperature in the range of 35° to 210° C.

7. The process according to claim 6 wherein the catalytic rearrangement of step (d) is conducted at a moderate temperature in the range of 35° to 110° C.

8. The process according to claim 1 wherein the catalytic rearrangement of step (d) is conducted under pressure of up to about 1000 psig.

9. The process according to claim 1 wherein said aqueous phase in step (c) is washed with inert solvent to remove sulfilimine.

10. The process according to claim 1 wherein said minor amount of succinimide in step (d) comprises 1 to 10% by weight of said neutral sulfilimine.

11. The process according to claim 1 wherein said organic phase containing neutral sulfilimine separated in step (c) is treated to recover essentially pure sulfilimine.

12. The process according to claim 11 wherein said treatment comprises the steps of:
   (a) removing solvent from said organic phase by distillation;
   (b) triturating the solid residue produced in step (a) with an inert organic solvent having a low solubility for said sulfilimine; and
   (c) filtering the mixture of step (b) to recover essentially pure solid sulfilimine.

13. The process according to claim 12 wherein said inert organic solvent is selected from the group consisting of hexane and heptane.

14. The process according to claim 11 wherein a minor amount of succinimide is mixed with said essentially pure sulfilimine prior to said catalytic rearrangement.

* * * * *